(12) United States Patent
Schmitt

(10) Patent No.: US 10,278,798 B2
(45) Date of Patent: May 7, 2019

(54) SYSTEM FOR THE PRESERVATION OF A PREDETERMINED DOSE OF LIQUID-BASED SUBSTANCE IN PARTICULAR DILUTED ANIMAL SEMEN

(71) Applicant: IMV TECHNOLOGIES, Saint Ouen sur Iton (FR)

(72) Inventor: Eric Schmitt, Villanies-la-Juhel (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 103 days.

(21) Appl. No.: 15/314,330

(22) PCT Filed: May 27, 2015

(86) PCT No.: PCT/FR2015/051396
§ 371 (c)(1),
(2) Date: Nov. 28, 2016

(87) PCT Pub. No.: WO2015/181496
PCT Pub. Date: Dec. 3, 2015

(65) Prior Publication Data
US 2017/0189156 A1 Jul. 6, 2017

(30) Foreign Application Priority Data
May 28, 2014 (FR) ..................................... 14 54894

(51) Int. Cl.
*A61D 19/00* (2006.01)
*A61D 19/02* (2006.01)
(Continued)

(52) U.S. Cl.
CPC ............ *A61D 19/024* (2013.01); *A01N 1/02* (2013.01); *A01N 1/0268* (2013.01); *A61D 19/00* (2013.01);
(Continued)

(58) Field of Classification Search
CPC .... A61D 19/00; A61D 19/022; A61D 19/024; A61F 17/425; A61F 17/43; A61F 17/435
See application file for complete search history.

(56) References Cited

U.S. PATENT DOCUMENTS

| 5,868,178 A | * | 2/1999 | Lecointe | ............. A61D 19/024 119/174 |
| 6,416,611 B1 | | 7/2002 | Saint-Ramon et al. | |

(Continued)

FOREIGN PATENT DOCUMENTS

| EP | 0873826 A2 | 10/1998 |
| EP | 0922451 A2 | 6/1999 |

(Continued)

OTHER PUBLICATIONS

FR 2810535 Translation.*
Copending U.S. Appl. No. 15/314,350, filed Nov. 28, 2016.

*Primary Examiner* — Carrie R Dorna
(74) *Attorney, Agent, or Firm* — Browdy and Neimark, P.L.L.C.

(57) ABSTRACT

The system comprises a straw and a liquid dilution medium. The straw comprises a tube (11) extending between a first end and a second end and comprises a gas-permeable, liquid-tight plug, said plug being arranged in the tube (11) in the vicinity of the first end of same and extending between a first end turned towards the first end of the tube (11) and a second end turned towards the second end of the tube (11). Said plug comprises an element (14) impregnated with a reagent (22) at least in the vicinity of a first end turned towards the second end of the tube (11). The liquid medium is provided to produce, by mixing, in predefined conditions, the liquid substance (21). The reagent (22) and the medium (27) are configured such that, when the substance (21)

(Continued)

comes into contact with the first end of the impregnated element (14), it forms a hydrogel.

14 Claims, 1 Drawing Sheet

(51) Int. Cl.
*A01N 1/02* (2006.01)
*A61D 19/04* (2006.01)
*A61K 35/52* (2015.01)

(52) U.S. Cl.
CPC ............ *A61D 19/02* (2013.01); *A61D 19/04* (2013.01); *A61K 35/52* (2013.01)

(56) References Cited

U.S. PATENT DOCUMENTS

2001/0014376 A1  8/2001  Saint-Ramon et al.
2002/0183653 A1  12/2002  Saint-Ramon et al.
2002/0188222 A1  12/2002  Saint-Ramon et al.
2009/0208566 A1  8/2009  Vigo et al.
2012/0301868 A1* 11/2012  Pascual ................ A01N 1/0231
                                                       435/2

FOREIGN PATENT DOCUMENTS

| EP | 2526768 A1 | 11/2012 |
| FR | 995878 A | 12/1951 |
| FR | 2771285 A1 | 5/1999 |
| FR | 2784572 A1 | 4/2000 |
| FR | 2810535 A1 | 12/2001 |
| FR | 2824255 A1 | 11/2002 |
| FR | 2824256 A1 | 11/2002 |
| GB | 669265 A | 4/1952 |
| WO | 2013076232 A1 | 5/2013 |

* cited by examiner

SYSTEM FOR THE PRESERVATION OF A PREDETERMINED DOSE OF LIQUID-BASED SUBSTANCE IN PARTICULAR DILUTED ANIMAL SEMEN

The invention generally concerns the preservation of a predetermined dose of liquid-based substance containing biological material. Such a substance is for example diluted animal semen.

More particularly, the invention concerns the straws for implementing such preservation.

It is known that these straws are conventionally formed by a thin tube, having for example an inner diameter of 1.6 or 2.5 mm, and by a stopper inserted in the thin tube.

In the filled state, the stopper is arranged close to a first end of the tube and the dose of liquid-based substance is arranged in the straw between the stopper and the second end of the tube.

In order to fill the straw, the first end of the tube, close to the stopper, is placed in communication with a vacuum source, while the second end is placed in communication with a vessel containing the substance to be introduced into the straw. The air initially contained between the stopper and the second end is sucked through the stopper while the substance moves forward into the tube unto it reaches the stopper, which it cannot pass because the stopper becomes liquid-tight.

If necessary, after filling, the straw is welded close to one or both of its ends and is stored cold.

In order to empty the straw, if necessary after cutting the welded end portions and thawing, a rod is inserted into the tube via the end closest to the stopper, until it bears against the stopper. Using this rod, the stopper is made to slide in the manner of a piston towards the end furthest from the stopper, so that the dose of substance initially contained in the straw is expelled through that end.

Straw stoppers are generally of the three-part type originally described in French patent 995,878, corresponding to British patent 669,265, i.e. formed by two plugs made from a fibrous substance enclosing a powder which, on contact with a liquid, is transformed into an impermeable paste or gel adhering to the wall of the tube so that the stopper is liquid-tight.

European patent application EP 0 873 726 proposes that the stopper be formed by a single-piece cylinder of hydrophobic microporous material French patent applications 2 771 285 and 2 784 572, to which American patent application US 2001/0014376 and American patent U.S. Pat. No. 6,416,611 correspond, propose that the stopper be constituted by a stiff insert perforated by a substantially coaxial orifice and a hydrophobic microporous membrane combined with the insert in order to seal the insert orifice on the inside.

French patent applications 2 824 255 and 2 824 256, to which American patent applications US 2002/0183653 and US 2002/0188222 correspond, propose to add to the stopper, besides the powder and fibres, non-absorbent elements, namely a core made from thermoplastic material, covered with a sleeve made from braided threads, and non-absorbent material in dispersed form, in the powder.

The invention is directed to limiting the loss, in the stopper of such a straw, of the product of interest contained in the liquid-based substance, for example spermatozoids if the substance is diluted semen.

To that end the invention provides a system for the preservation of biological material, characterized in that it comprises:

a straw for the preservation of a predetermined dose of liquid-based substance containing said biological material, comprising a tube extending between a first end and a second end and comprising a liquid-tight, gas-permeable stopper, which stopper is disposed in the tube close to its first end and extends between a first end facing towards the first end of the tube and a second end facing towards the second end of the tube, said stopper comprising a member impregnated with a reagent at least in the neighborhood of a first end facing towards the second end of the tube; and a liquid dilution extender to give by mixing, in predetermined conditions, said liquid-based substance;

said reagent and said liquid dilution extender being configured such that on contact of said substance with the first end of the impregnated member, it forms a hydrogel.

For example, the primary product contained in the dilution extender is an alginate in solution, and the reagent contained in the stopper of the straw is formed by multivalent canons.

It is known that in an aqueous medium, multivalent cations have the capacity to cross-link alginates.

Therefore, if the liquid-based substance contains an alginate, in contact with the second end of the stopper of the straw, the substance thickens and forms a matrix or network which cannot be traversed by the product of interest, for example spermatozoids, which cannot therefore penetrate into the stopper where it would be lost.

The system according to the invention thus makes it possible to limit the loss of the product of interest in the stopper of the straw.

It will be noted that it is possible to add an alginate to a liquid-based substance in a proportion such that the alginate can react with the multivalent cations as has just been indicated, without this addition influencing the viscosity of the liquid-based substance or else influencing that viscosity minimally. Therefore, this addition has little or no influence on the product of interest contained in the substance, for example spermatozoids. Similarly, this addition has little or no influence on the cooperation of the liquid-based substance with the straw, apart from the above-mentioned cross-linking of the alginate.

It will be noted that the impregnation of the stopper of the straw at least in the vicinity of the second end by multivalent cations is a relatively simple operation to carry out. The straw of the system according to the invention is thus simple, convenient and economic to produce.

According to advantageous features:

said multivalent cations are divalent cations;

said divalent cations comprise barium $Ba^{++}$ cations;

said divalent cations comprise calcium $Ca^{++}$ cations;

said stopper comprises two plugs made from a fibrous substance enclosing a sealing agent formed by a powder which, on contact with a liquid, transforms into an impermeable paste or gel adhering to the wall of the tube so that the stopper is liquid-tight;

in the stopper of the straw, the plug situated towards the second end of the tube forms said impregnated member, said first end of the impregnated member forming said second end of the stopper;

said stopper comprises a gas-permeable, liquid permeable barrier plug extending between a first end facing towards the first end of the tube and a second end facing towards the second end of the tube, the first end of the impregnated member and the second end of the barrier plug being disposed against each other;

the barrier plug is hydrophobic; and/or
said impregnated member is a plug entirely impregnated with divalent cations.

Advantageously, said liquid-based substance is diluted animal semen and said alginate is in a concentration comprised between 0.1 and 6 g/l; and still more advantageously in a concentration comprised between 2.5 and 5 g/l.

It will be noted that in the system according to the invention, it is possible for the hydrogel formed to be different from an alginate-cation multivalent matrix or network. For example, the primary product contained in the dilution extender is different from the alginates, for example a pectin, and/or the reagent contained in the stopper of the straw is different from multivalent cations, for example an add.

The disclosure of the invention will now be continued with the detailed description of embodiments, given below by way of illustrative and non-limiting example, with reference to the accompanying drawings, in which.

Figure 5:
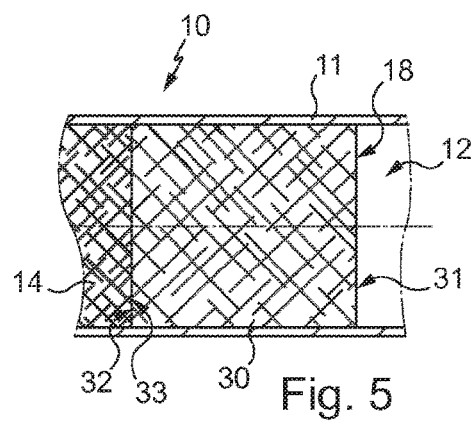
Figure 4:
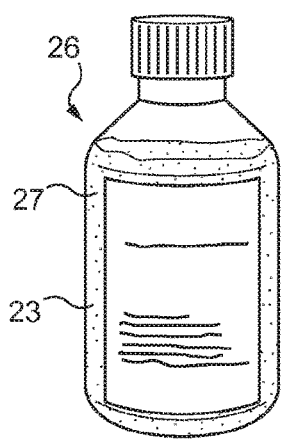
Figure 4:
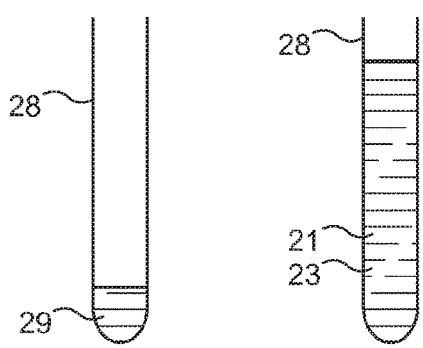

FIG. 4 diagrammatically illustrates a bottle containing a liquid dilution extender, a container containing pure animal semen and a container containing diluted animal semen obtained by dilution of that semen with that extender; and FIG. 5 is a partial view of a variant of the straw, in which the stopper further comprises a barrier plug.

Figure 1:
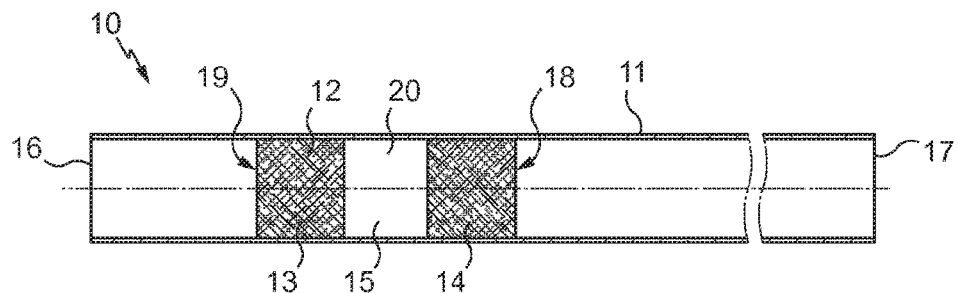
FIG. 1 is a diagrammatic view in longitudinal cross-section of a straw of a system according to the invention, in the empty state.

The straw 10 illustrated in FIG. 1 comprises a tube 11 and a stopper 12.

The tube 11 is conventionally made from extruded plastic material, here transparent, with an inside diameter for example of 1.6 or 2.5 mm and a length of the order of 133 mm.

The stopper 12 is of the three-part type, i.e. formed by two plugs 13 and 14 made from a fibrous substance, for example of braided threads, enclosing a sealing agent 20 formed by a powder (FIG. 1) which, on contact with a liquid, is capable of transforming into an impermeable paste or gel 15' (FIG. 2) adhering to the wall of the tube 11 so that the stopper 12 is liquid-tight.

In the initial state, shown in FIG. 1, the stopper 12 is disposed in the neighborhood of the end 16 of the tube 11 and it is provided that hi the filled state, the dose of liquid-based substance which must be preserved in the straw 10 is disposed between the stopper 12 and the end 17 of the tube 11 that is the furthest from the stopper 12.

In order to fill the straw 10, the end 16 is placed hi communication with a vacuum source while the end 17 is placed in communication with a vessel containing the substance to be introduced into the straw.

Figure 2:
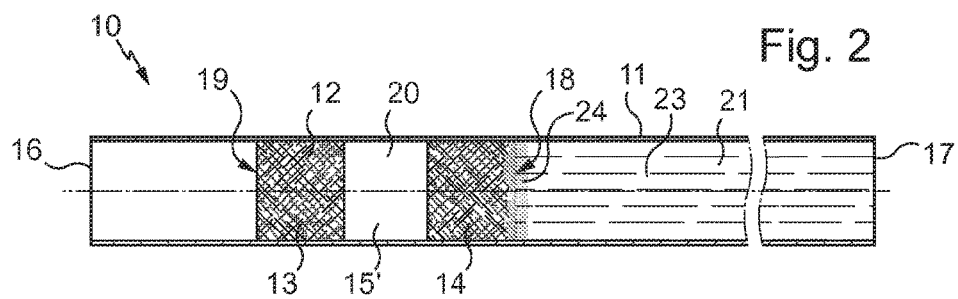
FIG. 2 is a view similar to FIG. 1 but showing the straw in the filled state.

The air initially contained between the stopper 12 and the end 17 is sucked through the stopper 12 while the substance 21 (FIG. 2) moves forward in the tube 11 until it encounters the stopper 12, by the end 18 thereof that faces towards the end 17 of the tube 11, that is to say the end of the stopper 12 that can be seen on the right in FIGS. 1 and 2.

The straw 10 is then in the filled state shown in FIG. 2.

If necessary, after filling, the straw is welded in the neighborhood of one or both of its ends 16 and 17 and is placed in cold storage.

To empty the straw 10, if necessary after cutting the welded end portions and thawing, there is inserted into the tube 11 a rod which comes to bear on the end 19 of the stopper 12 (which end is situated on the opposite side to the end 18).

Using this rod, the stopper 12 is made to slide in the manner of a piston towards the end 17 or the end which corresponds after cutting the welded portion, which causes the expulsion of the dose of substance 21 which had been introduced into the straw.

Figure 3:
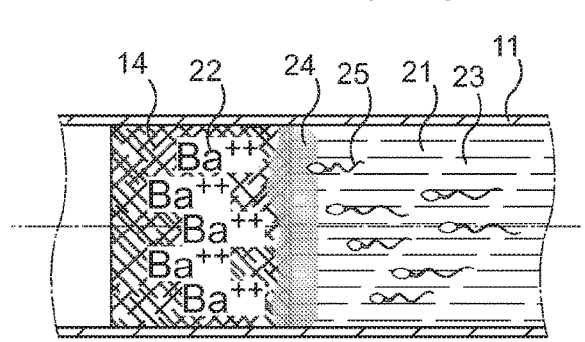
FIG. 3 is an enlargement of the part of FIG. 2 situated around the end of the stopper which can be seen to the right.

With reference to FIG. 3, a description will now be given in more detail of the plug 14 of the stopper 12 of the straw 10 and of the zone situated in the neighborhood of its end 18 when the straw 10 is in the filled state shown in FIG. 2.

The plug 14 is impregnated by divalent cations 22, here cations of barium, $Ba^{++}$.

The substance 21 here is diluted animal semen which contains an alginate.

It is known that in an aqueous medium, divalent cations such as the cations 22, have the capacity to cross-link alginates such as the alginate 23.

Thus, when the substance 21 came into contact with the end 18 of the stopper 12, the substance 21 thickened and formed a matrix or network 24.

The matrix or network 24 is such that the spermatozoids 25 contained in the substance 21 cannot traverse the matrix or network 24.

Therefore, the spermatozoids 25 cannot penetrate into the stopper 12, where they would be lost.

Here, the plug 14 is entirely impregnated with divalent cations 22, for reasons of convenience of manufacture.

For example, the plug 14 is manufactured from a section of a braided wick which had been soaked in a saturated solution of barium salt then removed from the bath and placed to dry before being cut up into sections one of which forms the plug 14.

As a variant, only the region near the end 18 is impregnated with divalent cations 22.

FIG. 4 shows a bottle 26 containing a dilution extender 27, a container 28 containing pure animal semen 29 and the same container 28 containing diluted animal semen, forming the substance 21, obtained by dilution of the pure animal semen 29 with the dilution extender 27.

It is clearly understood that the dilution extender 27 has not yet been mixed with pure semen, and is thus distinct from diluted semen.

The dilution extender 27 is for example that commercialized by the applicant under the name OPTIXCELL.

The dilution of the pure semen 29 by the extender 27 is carried out in predetermined conditions, in particular as regards the dilution ratio, that is to say the ratio between the total volume of the diluted semen 21 and the volume of the pure semen 29.

The dilution extender 27 contains the alginate 23, which has been selected to cross-link in contact with divalent cations 22 in order to form the matrix or network 24. which is thus a thickened zone of the diluted semen 21.

A range of concentration which is particularly suitable is the range from 0.1 g to 6 g of alginate per liter of dilution extender 27. A particularly advantageous range extends between 2.5 g/l and 5 g/l.

For example, with a concentration of alginate of the order of 2.5 g/l the proportion of liquid-based substance lost in the stopper 12 is from 3 to 4%; and with a concentration of the order of 5 g/l, the proportion of liquid-based substance lost in the stopper such as 12 is of the order of 1 à 3%.

It will be noted that this proportion of liquid lost in the stopper is determined by calculating the difference between the quantity of liquid-based substance introduced into the straw until the stopper 12 becomes fluid-tight and the quantity of liquid which the straw can return by sliding the stopper 12 as explained above.

It will be noted that in FIGS. 2 and 3, the matrix or network 24 is shown only in the vicinity of the end 18 of the stopper 12.

According to the concentration of the extender 27 in alginate, instead of having a localized presence of the matrix or network 24, as illustrated in FIGS. 2 and 3, the matrix or network may extend to a relatively great distance from the end 18 of the stopper 12.

The variant of the straw 10 shown in FIG. 5 is similar to the straw 10 shown in FIGS. 1 to 3 apart from the fact that the stopper 12 further comprises a barrier plug 30 towards the end 17 of the tube 11.

The barrier plug 30 extends between an end 31 facing towards the end 17 of the tube 11 and an end 32 facing towards the end 16 of the tube 11.

In the straw 10 shown in FIGS. 1 to 3 the end 18 of the stopper 12 facing towards the end 17 of the tube 11 forms part of the plug 14. hi the variant of the straw 10 shown in FIG. 5, the end 18 forms part of the barrier plug 30 and the plug 14 has, on the side facing towards the end 17, an end 33 distinct from the end 18.

The end 33 of the plug 14 and the end 32 of the barrier plug 30 are arranged against each other.

The barrier plug 30 is fibrous. It is gas-permeable and liquid-permeable.

The straw 10 shown in FIG. 5 is used in the same way as the straw 10 shown in FIGS. 1 to 3.

On filling, the substance 21 traverses the barrier plug 30 and encounters the plug 14 by its end 33 that faces towards the end 17 of the tube 11. In the same way as for the straw 10 shown in FIGS. 1 to 3, the substance 21 thickens and forms the matrix or network 24.

The barrier plug 30 enables the matrix or network 24 to remain in the stopper 12: the barrier plug 30 prevents the passage of the matrix or network 24 to the substance 21.

The barrier plug 30 is here a braid formed by threads arranged in a core and a cover surrounding the core.

Each thread is hydrophobic. Therefore, the barrier plug 30 is hydrophobic, and thus has a water-repellant effect.

This repellant effect does not prevent the substance 21 from passing through the baffler plug 30 and reaching the impregnated plug 14, since in practice the substance 21 comes up against the stopper 12 with a certain speed.

During the passage of the substance 21 into the barrier plug 30, the threads forming it do not absorb liquid; and after the passage of the substance 21 is blocked by the stopper 12, the barrier plug 30 does not keep the liquid situated in its interstices but returns it into the dose of liquid substance situated between the end 31 of the baffler plug 30 and the end 17 of the tube 11.

As a result, there is no consumption, or very reduced consumption, of liquid substance by the barrier plug 30.

In a variant not illustrated, in particular when the concentration of alginate in the dilution extender 27 is relatively high, the three-part stopper 12 is replaced by a stopper formed only by a plug such as the plug 14.

In a variant not illustrated, the stopper 12 is arranged differently, for example made from a one-piece cylinder of hydrophobic microporous material such as described in European patent application EP 0 873 726.

In variants not illustrated, the divalent cations 22 formed by barium ions $Ba^{++}$ are replaced by other divalent cations, for example calcium $Ca^{++}$ or magnesium $Mg^{++}$ cations.

In variants not illustrated, the divalent cations 22 are replaced by multivalent cations other than divalent ones, for example trivalent cations such aluminum $Al^{+++}$ or chromium $Cr^{+++}$ cations.

In variants not illustrated, the alginate-multivalent an matrix or network 24 is replaced by another hydrogel, that is to say a network or matrix of polymer chains swollen by the liquid-based substance, for example a pectin-multivalent cation matrix or network (the alginate of the dilution extender is replaced by pectin); and/or the reagent impregnating a member of the stopper is different from multivalent cations, for example an acid.

In other variants not illustrated, the liquid-based substance containing the biological material is different from diluted animal semen, for example a preservation medium containing embryos.

Numerous other variants are possible according to circumstances, and in this connection it is to be noted that the invention is not limited to the examples described and shown.

The invention claimed is:

1. A system for the preservation of biological material, characterized in that it comprises
   a straw for the preservation of a predetermined dose of a liquid-based substance containing said biological material, the straw having an initial empty state and a filled state and comprising a tube extending between a first end and a second end and comprising a liquid-tight, gas-permeable stopper, which stopper is disposed in the tube close to its first end and extends between a first end facing towards the first end of the tube and a second end facing towards the second end of the tube, said stopper comprising, in the initial empty state of the straw, a member impregnated with a reagent at least in the neighborhood of a first end facing towards the second end of the tube; and
   a liquid dilution extender to give by mixing with at least the biological material, in predetermined conditions, said liquid-based substance;
   said reagent and said liquid dilution extender being configured such that on contact of said substance with the first end of the impregnated member, a hydrogel is formed in the liquid-based substance outside the stopper.

2. A system according to claim 1, characterized in that said reagent is formed by multivalent cations.

3. A system according to claim 2, characterized in that said multivalent cations are divalent cations.

4. A system according to claim 3, characterized in that said divalent cations comprise barium $Ba^{++}$ cations.

5. A system according to claim 3, characterized in that said divalent cations comprise calcium $Ca^{++}$ cations.

6. A system according to claim 1, characterized in that said stopper comprises two plugs made from a fibrous substance enclosing a sealing agent formed by a powder which, on contact with a liquid, transforms into an impermeable paste or gel adhering to a wall of the tube so that the stopper is liquid-tight.

7. A system according to claim 6, characterized in that, in the stopper of the straw, a one of the two plugs that is situated towards the second end of the tube forms said impregnated member, said first end of the impregnated member forming said second end of the stopper.

8. A system according to claim 1, characterized in that said stopper comprises a gas-permeable, liquid permeable barrier plug extending between a first end facing towards the first end of the tube and a second end facing towards the second end of the tube, the first end of the impregnated member and the second end of the barrier plug being disposed against each other.

9. A system according to claim 8, characterized in that the barrier plug is hydrophobic.

10. A system according to claim 1, characterized in that said reagent is formed by divalent cations and said impregnated member is a plug entirely impregnated with the divalent cations.

11. A system according to claim 1, characterized in that said liquid dilution extender contains an alginate in solution.

12. A system according to claim 11, characterized in that said liquid-based substance is diluted animal semen and said alginate is in a concentration comprised between 0.1 and 6 g/l.

13. A system according to claim 12, characterized in that said alginate is in a concentration comprised between 2.5 and 5 g/l.

14. A system according to claim 1, characterized in that said hydrogel is an alginate-multivalent cation matrix or network.

* * * * *